(12) United States Patent
Liu et al.

(10) Patent No.: US 12,029,892 B2
(45) Date of Patent: Jul. 9, 2024

(54) APPARATUS FOR TREATING TINNITUS THROUGH STIMULATING MULTIPLE ACUPOINTS WITH MULTI-ELECTRODE ELECTRIC PULSE BASED ON BLUETOOTH CONTROL AND ACUPOINT STIMULATING METHOD USING THE SAME

(71) Applicant: HEFEI AI-NATURALISM ELECTRONIC TECHNOLOGY CO., LTD., Anhui (CN)

(72) Inventors: Yehai Liu, Anhui (CN); Chongxian Yu, Anhui (CN); Jing Wu, Anhui (CN); Jinjin Yuan, Anhui (CN); Yanxun Han, Anhui (CN); Renjun Hua, Anhui (CN); Weipeng Liu, Anhui (CN); Xinxin Xu, Anhui (CN); Zhaoxuan Lu, Anhui (CN)

(73) Assignee: HEFEI AI-NATURALISM ELECTRONIC TECHNOLOGY CO., LTD., Hefei (CN)

( * ) Notice: Subject to any disclaimer, the term of this patent is extended or adjusted under 35 U.S.C. 154(b) by 386 days.

(21) Appl. No.: 17/374,167

(22) Filed: Jul. 13, 2021

(65) Prior Publication Data
US 2021/0370046 A1    Dec. 2, 2021

Related U.S. Application Data

(63) Continuation of application No. PCT/CN2019/120882, filed on Nov. 26, 2019.

(30) Foreign Application Priority Data

Mar. 30, 2019 (CN) .......................... 201910259376.7

(51) Int. Cl.
*A61N 1/04* (2006.01)
*A61N 1/36* (2006.01)
*H02J 7/00* (2006.01)

(52) U.S. Cl.
CPC ......... *A61N 1/0408* (2013.01); *A61N 1/0492* (2013.01); *A61N 1/36034* (2017.08); *H02J 7/0047* (2013.01)

(58) Field of Classification Search
CPC ................ A61N 1/0408; A61N 1/0492; A61N 1/36034; H02J 7/0047; H02J 2310/23;
(Continued)

(56) References Cited

U.S. PATENT DOCUMENTS 9,415,220 B1 * 8/2016 Spinelli ............. A61N 1/36036
10,471,276 B2 * 11/2019 Beckner ............... A61B 5/0816
(Continued)

FOREIGN PATENT DOCUMENTS

CN          1083403 A      3/1994
CN       20170091935 A     8/2017
(Continued)

*Primary Examiner* — Carl H Layno
*Assistant Examiner* — Jane C Kalinock (57) ABSTRACT

An apparatus for treating tinnitus through stimulating multiple acupoints with a multi-electrode electric pulse. A control terminal controls a first MCU micro-control module and the second MCU micro-control module to allow the second MCU micro-control module to output a variety of different pulse signals, and the different pulse signals are respectively output to an electric-pulse output circuit and an electric-pulse conversion circuit. The pulse signal output to the electric-pulse output circuit is a carrier signal. The pulse signal output to the electric-pulse conversion circuit is converted to a modulating wave by the electric-pulse conversion circuit. The modulating wave and the carrier signal are both output to the electrical-pulse output circuit. After a modulation, a transcutaneous electric-pulse stimulation sig- (Continued)

nal is output by an output port, and is transmitted to an electrode sheet attached to the corresponding acupoint on human body through an electrode wire to stimulate the acupoint.

12 Claims, 10 Drawing Sheets

(58) Field of Classification Search
CPC .... A61H 39/00; A61H 39/002; A61B 5/0532; Y10S 128/907
USPC .......................................................... 607/55
See application file for complete search history.

(56) References Cited

U.S. PATENT DOCUMENTS

| | | | |
|---|---|---|---|
| 2006/0074337 A1* | 4/2006 | Yoo ........................ | A61H 39/02 |
| | | | 600/548 |
| 2007/0032827 A1 | 2/2007 | Katims | |
| 2017/0128017 A1* | 5/2017 | Zheng .................. | A61B 5/6898 |
| 2018/0042813 A1* | 2/2018 | Chiang ................ | A61B 5/4854 |
| 2020/0038658 A1* | 2/2020 | Tyler ..................... | A61M 21/02 |

FOREIGN PATENT DOCUMENTS

| CN | 207477800 U | 6/2018 |
|---|---|---|
| CN | 108578891 A | 9/2018 |
| CN | 208130251 U | 11/2018 |
| CN | 109821151 A | 5/2019 |

* cited by examiner

APPARATUS FOR TREATING TINNITUS THROUGH STIMULATING MULTIPLE ACUPOINTS WITH MULTI-ELECTRODE ELECTRIC PULSE BASED ON BLUETOOTH CONTROL AND ACUPOINT STIMULATING METHOD USING THE SAME

CROSS-REFERENCE TO RELATED APPLICATIONS

This application is a continuation of International Patent Application No. PCT/CN2019/120882, filed on Nov. 26, 2019, which claims the benefit of priority from Chinese Patent Application No. 201910259376.7, filed on Mar. 30, 2019. The content of the aforementioned applications, including any intervening amendments thereto, is incorporated herein by reference in its entirety.

TECHNICAL FIELD

This application relates to medical treatment, and more particularly to an apparatus for treating tinnitus through stimulating multiple acupoints with a multi-electrode electric pulse based on Bluetooth control and an acupoint stimulating method using the same.

BACKGROUND

Tinnitus is a subjective symptom in which the patient feels there is sound in the ear or intracranial region in the absence of a sound stimulation or electrical stimulation in the surrounding environment, and may be accompanied with adverse psychological reactions such as upset, irritation, inability to concentrate, sleep disorders depression and anxiety. The reported prevalence of tinnitus is 5% to 18%, and 15.2% of adult patients have experienced tinnitus lasting for at least 3 months. An early survey of 3000 people in Germany showed that the prevalence of tinnitus was 13%. Later, Henry reviewed the literature before 2005 and found that the prevalence of tinnitus was about 10%-15%. In the United States, Loprinzi et al conducted a survey on 963 adolescents (aged 12-19 years old) and 473 older adults (aged 70-85 years old), and the weighted prevalence of tinnitus was 8.9% and 25.3% for adolescents and older adults, respectively. In China, it is reported that 10% of people have experienced tinnitus; 5% of tinnitus patient have sought medical help due to the tinnitus; the tinnitus has severely affected the daily life of 2% of tinnitus patient; and 0.5% of the patient almost become disabled due to the severe tinnitus. Tinnitus seriously affects the health-related quality of life (QOL), and may impact the economy.

Tinnitus is divided into primary tinnitus and secondary tinnitus. The secondary tinnitus is related to a certain underlying cause (except for sensorineural deafness) or a diagnosable physiological state, and can be alleviated through treating the cause. The primary tinnitus is idiopathic tinnitus with or without sensorineural hearing loss, and its pathogenesis is not clear. The pathogenic factors of the tinnitus are complicated, and the tinnitus can be treated through different ways such as psychological therapy, wearing hearing aids and special therapeutic acoustic devices, cognitive behavioral therapy (CBT), drug therapy and transcranial magnetic stimulation (TMS). Although these therapies can improve tinnitus and help patients to adapt to tinnitus, the therapeutic effect is not satisfactory. Traditional Chinese medicine has also carried out long-term explorations on the prevention and treatment of tinnitus. The pathogenesis, clinical diagnosis and treatment of tinnitus have been deeply understood through the unique dialectic system of traditional Chinese medicine. Some effective methods are recorded in ancient books, and have also been summarized in the clinic. Acupuncture is an effective way to treat tinnitus, and has attracted extensive attention in the medical science.

Acupuncture at specific acupoint points has a good treating effect on tinnitus, but this therapy also has some problems. Acupuncture treatment requires high technique, and the treatment must be operated by an experienced therapist to avoid safety problems. Meanwhile, the acupuncture treatment many cause some adverse events such as bleeding, hematoma, pain at the acupuncture site, fatigue, headache, fainting and local skin irritation. Furthermore, the patients have to go to the medical institution for treatment many times due to the long course period of treatment, increasing the transportation cost and the inconvenience. In addition, some patients are afraid of acupuncture treatment. The above factors will limit the clinical application of the acupuncture treatment.

SUMMARY

To solve the above-mentioned problems, the present disclosure provides an apparatus for treating tinnitus through stimulating multiple acupoints with a multi-electrode electric pulse based on Bluetooth control, which comprises:
 a control terminal;
 a main body;
 an electrode wire; and
 an electrode sheet group connected to the electrode wire;
 wherein the electrode sheet group comprises at least three electrode sheets;
 the main body comprises a control module, a power supply module and an output module; the power supply module and the output module are electrically connected to the control module, respectively; the control module comprises a first microcontroller unit (MCU) micro-control circuit and a Bluetooth communication circuit; the Bluetooth communication circuit is electrically connected to the first MCU micro-control circuit; the first MCU micro-control circuit is connected to the power supply module; the first MCU micro-control circuit is wirelessly connected to the control terminal through the Bluetooth communication circuit;
 the output module comprises a second MCU micro-control circuit, a voltage regulation circuit, an electric-pulse conversion circuit, an electric-pulse output circuit and an output port;
 the second MCU micro-control circuit is electrically connected to the first MCU micro-control circuit, the voltage regulation circuit, the electric-pulse conversion circuit and the electric-pulse output circuit; the voltage regulation circuit is electrically connected to the electric-pulse output circuit and the electric-pulse conversion circuit; the electric-pulse output circuit is electrically connected to the electric-pulse conversion circuit and the output port; and the electrode wire is connected to the output port;
 the first MCU micro-control circuit is configured to control the second MCU micro-control circuit to output a pulse signal to the electric-pulse conversion circuit, so as to output a modulating wave through conversion by the electric-pulse conversion circuit; the pulse signal output from the second MCU micro-control circuit to the electric-pulse output circuit is a carrier signal; a transcutaneous electric-pulse stimulation signal output by the electric-pulse output circuit is an electric pulse of the carrier signal after modulated by the modulating wave;

the modulating wave is a low-frequency pulse signal which is mainly characterized by frequency $f_{low}$, period $T_{low}$, and pulse width $\tau_{low}$;

the carrier signal is a mid-frequency pulse signal; the mid-frequency pulse signal is a bipolar signal; the mid-frequency pulse signal is mainly characterized by frequency $f_{mid}$, period $T_{mid}$, pulse width $\tau_{mid}$, time difference $\Delta\tau$ between an end of a negative mid-frequency pulse signal and a start of a positive pulse and a mid-frequency pulse signal duty cycle D;

the transcutaneous electric-pulse stimulation signal is a rectangular voltage pulse or a rectangular current pulse;

the transcutaneous electric-pulse stimulation signal is characterized by $f_{low}$, $T_{low}$, $\tau_{low}$, $f_{mid}$, $T_{mid}$, $\tau_{mid}$, $\Delta\tau$, the mid-frequency pulse signal duty cycle D, maximum amplitude $A_{max}$ and minimum amplitude $A_{min}$;

parameters meet the following conditions:

$$f_{low} = 0.1 \sim 100 \text{ Hz}; f_{low} = \frac{1}{T_{low}};$$

$$f_{mid} = 1 \sim 100 \text{ KHz}; f_{mid} = \frac{1}{T_{mid}};$$

$f_{low}=nf_{mid}$; wherein n is any positive integer;

$\tau_{low} > 2\tau_{mid} + \Delta\tau$;

wherein $\Delta\tau = T_{mid}(1-2D)$; $\tau_{low}=0.1\sim1$ ms; $\tau_{mid}=D \cdot T_{mid}$; $D=1\%\sim50\%$;

$$\frac{A_{min}}{A_{max}} = 0 \sim 1;$$

and the control terminal is configured to control the first MCU micro-control circuit and the second MCU micro-control circuit to allow the electric-pulse output circuit to output a corresponding transcutaneous electric-pulse stimulation signal to an electrode sheet of the at least three electrode sheets according to a time series combination.

In some embodiments, the electrode sheet group comprises an electrode sheet A, an electrode sheet B and an electrode sheet C; the time series combination is shown as follows:

$[\tau_{AB}-\tau-\tau_{BC}-\tau-\tau_{AC}-\tau]_{T_0}$;   time series 1:

$[|\tau_{AB}-\tau|_{T_1}-|\tau_{BC}-\tau|_{T_2}-|\tau_{AC}-\tau|_{T_3}]$; and   time series 2:

$[|\tau_{AB}-\tau|_{T_1}-|\tau_{AC}-\tau|_{T_3}-|\tau_{BC}-\tau|_{T_2}]$;   time series 3:

wherein $\tau_{AB}$ is time for the electrode sheet A and the electrode sheet B to output an electric pulse, and is 3-5 seconds;

$\tau_{BC}$ is time for the electrode sheet B and the electrode sheet C to output an electric pulse, and is 3-5 seconds;

$\tau_{AC}$ is time for the electrode sheet A and the electrode sheet C to output an electric pulse, and is 3-5 seconds;

$\tau$ is time when the electrode sheet A, the electrode sheet B and the electrode sheet C have no output, and is 1-2 seconds;

$T_0$ is time of an output loop of the electrode sheet A, the electrode sheet B and the electrode sheet C in sequence in the time series 1, and is 45-90 min;

$T_1$ is time of an output loop of the electrode sheet A and the electrode sheet B in the time series 2 and the time series 3, and is 15-30 min;

$T_2$ is time of an output loop of the electrode sheet B and the electrode sheet C in the time series 2 and the time series 3, and is 15-30 min; and $T_3$ is time of an output loop of the electrode sheet A and the electrode sheet C in the time series 2 and the time series 3, and is 15-30 min.

In some embodiments, $f_{low}=50$ Hz; $f_{mid}=1$ KHz; n=20; $T_{low}=20$ ms; $T_{mid}=1$ ms; $\tau_{low}=800$ us; $\tau_{mid}=200$ us; D=20%; and $\Delta\tau=300$ us.

In some embodiments, the power supply module comprises a charging port, a charging management circuit, a rechargeable battery, a power path management circuit and a power conversion circuit electrically connected in sequence; the power supply module further comprises a charging indication circuit; the charging indication circuit is electrically connected to the charging management circuit; and the power path management circuit is electrically connected to the first MCU micro-control circuit.

In some embodiments, the control module further comprises a power measuring circuit, a switch circuit and a work indication circuit; the power measuring circuit, the switch circuit and the work indication circuit are electrically connected to the first MCU micro-control circuit; and the power measuring circuit is electrically connected to the rechargeable battery.

In some embodiments, the control terminal is a smart phone.

An acupoint stimulating method using the apparatus mentioned above, comprising:

placing three electrode sheets of the apparatus on Zhongzhu acupoint, Tinggong acupoint and Yifeng acupoint of human body, respectively; and outputting, by the electric-pulse output circuit, a corresponding transcutaneous electric-pulse stimulation signal to an electrode sheet of the three electrode sheets according to a time series combination.

The beneficial effects of the present disclosure are described as follows.

The control terminal controls the first MCU micro-control module and the second MCU micro-control module, such that the second MCU micro-control module outputs a variety of different pulse signals, and the different pulse signals are respectively output to the electric-pulse output circuit and the electric-pulse conversion circuit. The pulse signal output to the electric-pulse output circuit is the carrier signal. The pulse signal output to the electric-pulse conversion circuit is converted to the modulating wave by the electric-pulse conversion circuit. The modulating wave and the carrier signal are both output to the electrical-pulse output circuit. After being modulated, the transcutaneous electric-pulse stimulation signal is output by the output port, and is transmitted to the electrode sheet through the electrode wire. The electrode sheet is attached to the corresponding acupoint on the skin of human body, such that the transcutaneous electric-pulse stimulation signal can stimulate the acupoint to treat tinnitus.

When the ratio of the minimum amplitude to the maximum amplitude of the transcutaneous electric-pulse stimulation signal is 0:

$$\frac{A_{min}}{A_{max}} = 0,$$

the transcutaneous electric-pulse stimulation signal is the low-frequency transcutaneous electric-pulse stimulation signal. When the ratio of the minimum amplitude to the maximum amplitude of the transcutaneous electric-pulse stimulation signal is non-zero:

$$\frac{A_{min}}{A_{max}} \neq 0,$$

the transcutaneous electric-pulse stimulation signal is the mid-frequency transcutaneous electric-pulse stimulation signal.

$$\frac{A_{min}}{A_{max}} = 0$$

can meet the stimulation needs of people with normal body shape. With respect to the crowd, it should be adjusted to $$\frac{A_{min}}{A_{max}} \neq 0,$$

and the low-frequency transcutaneous electric-pulse stimulation signal is replaced by the mid-frequency transcutaneous electric-pulse stimulation signal to deepen the action area, so as to maintain the effect of the low frequency parameter and provide a better stimulation effect.

In addition, the time series combination of the mid-frequency or low-frequency trans cutaneous electric-pulse stimulation signal of the above-mentioned multi-electrode sheet can simplify the treatment process and optimize the treatment effect.

The characteristic parameters of the above-mentioned carrier signal or modulating wave is controlled by the control terminal, and the carrier signal or the modulating wave is sent to the first MCU micro control module and the second MCU micro control module through the Bluetooth communication circuit to control the output of the mid-frequency or low-frequency transcutaneous electric-pulse stimulation signal. The stimulation intensity of the mid-frequency or low-frequency transcutaneous electric-pulse stimulation signal is also sent to the first MCU micro-control module and the second MCU micro-control module by the control terminal through the Bluetooth communication circuit, and then achieved by the second MCU micro-control module through controlling the voltage regulation circuit.

The present disclosure combines the modern electronic technology with the meridian and acupuncture in traditional Chinese medicine to provide a non-invasive treatment. The simulated "acupuncture and moxibustion therapy" in the treatment of tinnitus can promote blood circulation and alleviate tinnitus. According to the symptoms and physical signs of the patient, the corresponding acupoints are selected and stuck with electrode sheets. The Bluetooth communication technology can provide a low-frequency or mid-frequency pulse stimulation therapy, and controls the stimulation scheme, stimulation intensity and treatment time. The therapeutic apparatus provided herein is safe, convenient and effective, and is promising in clinical application.

DETAILED DESCRIPTION OF EMBODIMENTS

Figure 1:
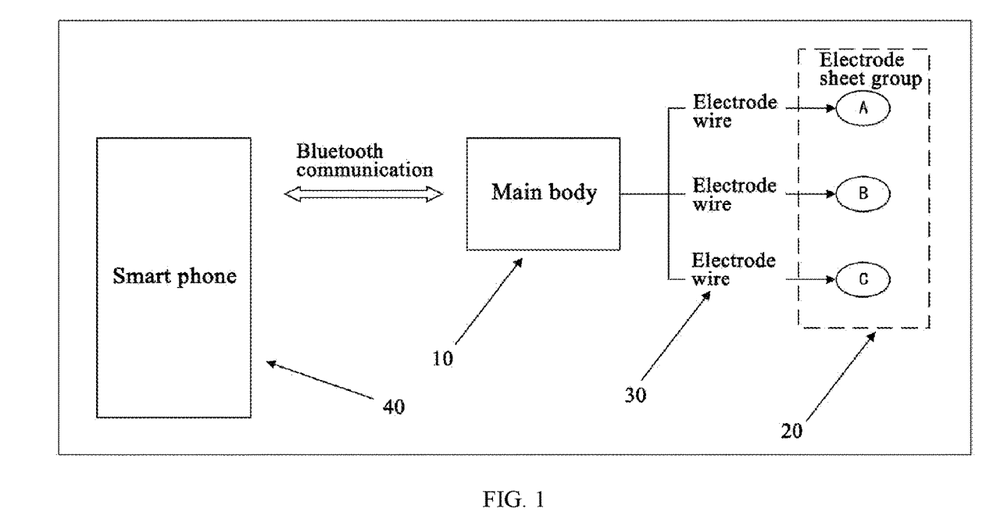
FIG. 1 schematically depicts a structure of a therapeutic apparatus in accordance with an embodiment of the present disclosure.

As shown in FIG. 1, the present disclosure provides an apparatus for treating tinnitus through stimulating multiple acupoints with a multi-electrode electric pulse based on Bluetooth control. The apparatus includes a main body 10, a smart phone 40 as a control terminal, an electrode wire 30 and an electrode sheet group 20 connected to the electrode wire 30. The electrode wire 30 is connected to the main body 10. The electrode sheet group 20 includes an electrode sheet A, an electrode sheet B and an electrode sheet C.

Figure 2:
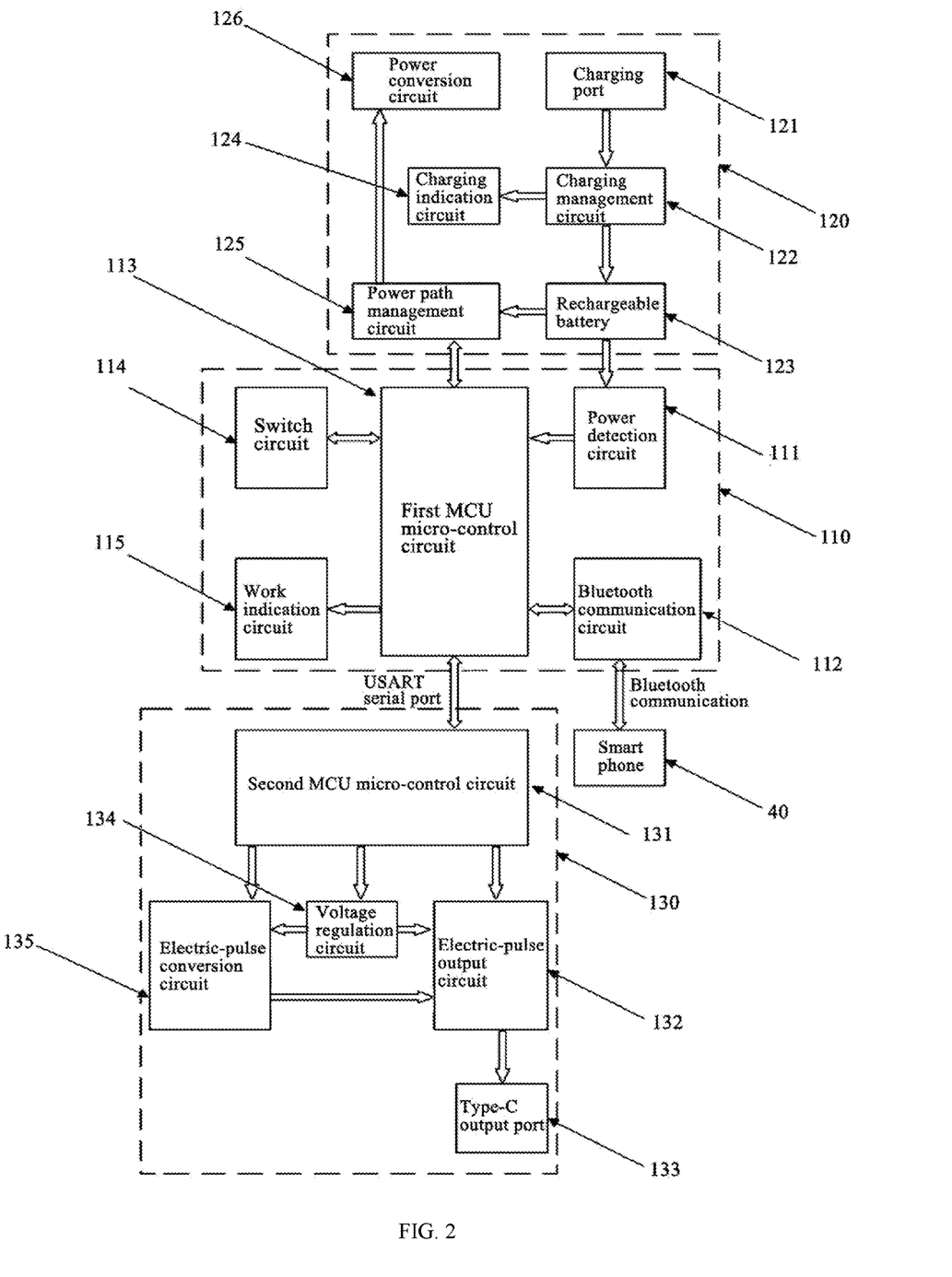
FIG. 2 is a circuit diagram of a main body in accordance with an embodiment of the present disclosure.

As shown in FIG. 2, the main body 10 includes a control module 110, and a power supply module 120 and an output module 130 electrically connected to the control module 110, respectively.

The power supply module 120 includes a charging port 121, a charging management circuit 122, a rechargeable battery 123, a power path management circuit 125 and a power conversion circuit 126 electrically connected in sequence, and the power supply module 120 further includes a charging indication circuit 124 electrically connected to the charging management circuit 122.

The output module 130 includes a second microcontroller unit (MCU) micro-control circuit 131, an electric-pulse output circuit 132, a Type-C output port circuit 133, a voltage regulation circuit 134, and an electric-pulse conversion circuit 135. The electric-pulse output circuit 132, the voltage regulation circuit 134 and the electric-pulse conversion circuit 135 are respectively electrically connected to the second MCU micro-control circuit 131. The voltage regulation circuit 134 is electrically connected to the electric-pulse output circuit 132 and the electric-pulse conversion circuit 135. The electric-pulse output circuit 132 is electrically connected to the electric-pulse conversion circuit 135. The Type-C output port circuit 133 is electrically connected to the electric-pulse output circuit 132. The electrode wire 30 is connected to the Type-C output port circuit 133.

The control module 110 includes a first MCU micro-control circuit 113, a power detection circuit 111, a Bluetooth communication circuit 112, a switch circuit 114 and a work indication circuit 115. The power detection circuit 111, the Bluetooth communication circuit 112, the switch circuit 114 and the work indication circuit 115 are respectively electrically connected to the first MCU micro-control circuit 113. The first MCU micro-control circuit 113 is electrically connected to the power path management circuit 125 and the second MCU micro-control circuit 131. The first MCU micro-control circuit 113 and the second MCU micro-control circuit 131 realize communication control through a universal synchronous/asynchronous receiver/transmitter (USART) serial port. The power detection circuit 111 is electrically connected to the rechargeable battery 123.

Figure 3:
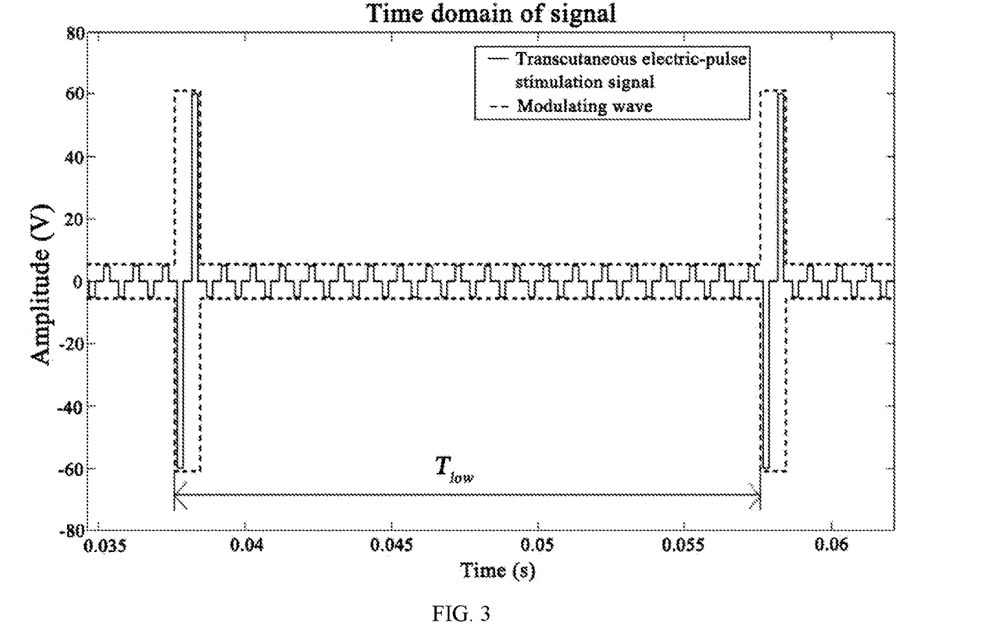
FIG. 3 is a schematic diagram of a mid-frequency transcutaneous electric-pulse stimulation signal in accordance with an embodiment of the present disclosure.
Figure 4:
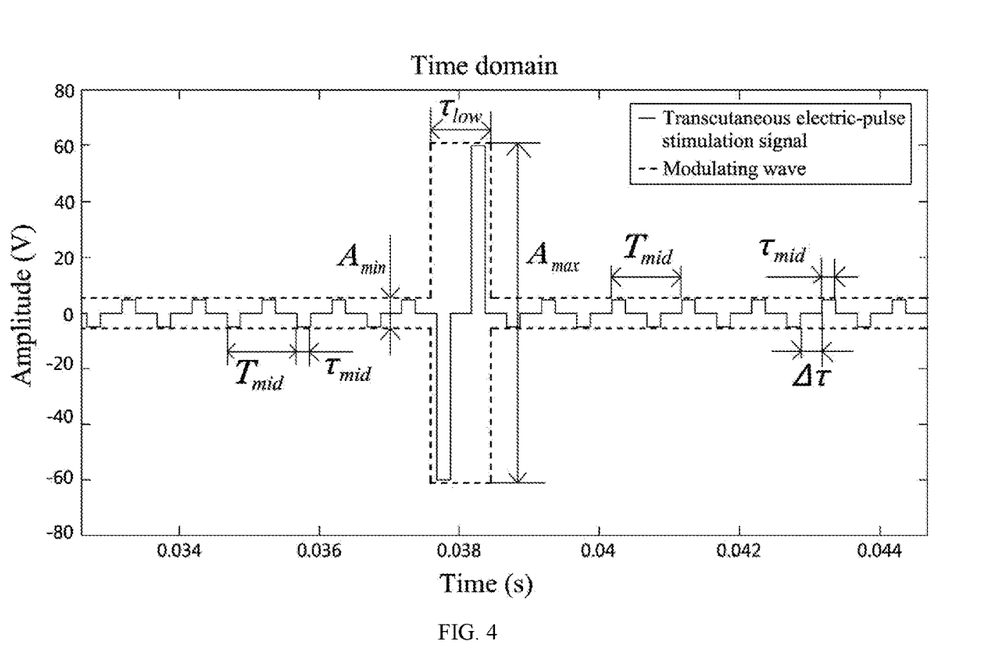
FIG. 4 is a partial enlarged view of FIG. 3.

As shown in FIGS. 3-4, the smart phone 40 communicates with the Bluetooth communication circuit 112 and transmits a control signal to the first MCU micro-control circuit 113. The first MCU micro-control circuit 113 controls the second MCU micro-control circuit 131 to output a pulse signal to the electric-pulse conversion circuit 135. After the conversion by the electric-pulse conversion circuit 135, the electric-pulse conversion circuit 135 outputs a modulating wave as shown in the dotted line in FIGS. 3 and 4.

The pulse signal output from the second MCU micro-control circuit 131 to the electric-pulse output circuit 132 is a carrier signal. The electric-pulse output circuit 132 outputs a low-frequency or a mid-frequency transcutaneous electric-pulse stimulation signal, which is an electric pulse of the carrier signal after modulated by the modulating wave. The solid lines shown in FIGS. 3 and 4 are the mid-frequency transcutaneous electric-pulse stimulation signal (the low-frequency transcutaneous electric-pulse stimulation signal is not shown). The Type-C output port circuit 133 selects and switches the output signal, and outputs it to the electrode wire 30 and the electrode sheet group 20. The output signal is transmitted to the human skin through the electrode sheet A, the electrode sheet B and the electrode sheet C those are attached to the human skin.

The second MCU micro-control circuit 131 controls the voltage regulation circuit 134 to output voltages of different intensities, provides a high voltage source for the electric-pulse output circuit 132 and the electric-pulse conversion circuit 135, and controls the intensity of the mid-frequency or low-frequency transcutaneous electric-pulse stimulation signal through the smart phone 40.

The modulating wave is a low-frequency pulse signal, and the low-frequency pulse signal is mainly characterized by frequency $f_{low}$, period $T_{low}$ and pulse width $\tau_{low}$.

The carrier signal is a mid-frequency pulse signal, and the mid-frequency pulse signal is a bipolar signal. The mid-frequency pulse signal is mainly characterized by frequency $f_{mid}$, period $T_{mid}$, pulse width $\tau_{mid}$, time difference $\Delta\tau$ between an end of a negative mid-frequency pulse signal and a start of a positive pulse and a mid-frequency pulse signal duty cycle D.

The mid-frequency or low-frequency transcutaneous electric-pulse stimulation signal is a rectangular voltage pulse or a rectangular current pulse.

The main characteristic parameters of mid-frequency or low-frequency transcutaneous electric-pulse stimulation signal include $f_{low}$, $T_{low}$, $\tau_{low}$, $f_{mid}$, $T_{mid}$, $\tau_{mid}$, $\Delta\tau$, the mid-frequency pulse signal duty cycle D, maximum amplitude $A_{max}$ and minimum amplitude $A_{min}$;

Those parameters meet the following conditions.

$$f_{low} = 0.1 \sim 100 \text{ Hz}; f_{low} = \frac{1}{T_{low}};$$

$$f_{mid} = 1 \sim 100 \text{ KHz}; f_{mid} = \frac{1}{T_{mid}};$$

$f_{low} = nf_{mid}$; where n is any positive integer;

$\tau_{low} > 2\tau_{mid} + \Delta\tau$; where $\Delta\tau = T_{mid}(1-2D)$; $\tau_{low} = 0.1 \sim 1$ ms; $\tau_{mid} = D \cdot T_{mid}$; $D = 1\% \sim 50\%$;

$$\frac{A_{min}}{A_{max}} = 0 \sim 1.$$

In some embodiments, $f_{low} = 50$ Hz; $f_{mid} = 1$ KHz; $n=20$; $T_{low} = 20$ ms; $T_{mid} = 1$ ms; $\tau_{low} = 800$ us; $\phi_{mid} = 200$ us; $D=20\%$; $\Delta\tau = 300$ us.

It should be noted that FIGS. 3 and 4 of this embodiment only show schematic diagrams of the mid-frequency transcutaneous electric-pulse stimulation signal, that is, when the ratio of the minimum amplitude to the maximum amplitude is non-zero:

$$\frac{A_{min}}{A_{max}} \neq 0.$$

When the ratio of the minimum amplitude to the maximum amplitude of the transcutaneous electric-pulse stimulation signal is 0:

$$\frac{A_{min}}{A_{max}} = 0,$$

the transcutaneous electric-pulse stimulation signal is the low-frequency transcutaneous electric-pulse stimulation signal (not shown).

Figure 5:
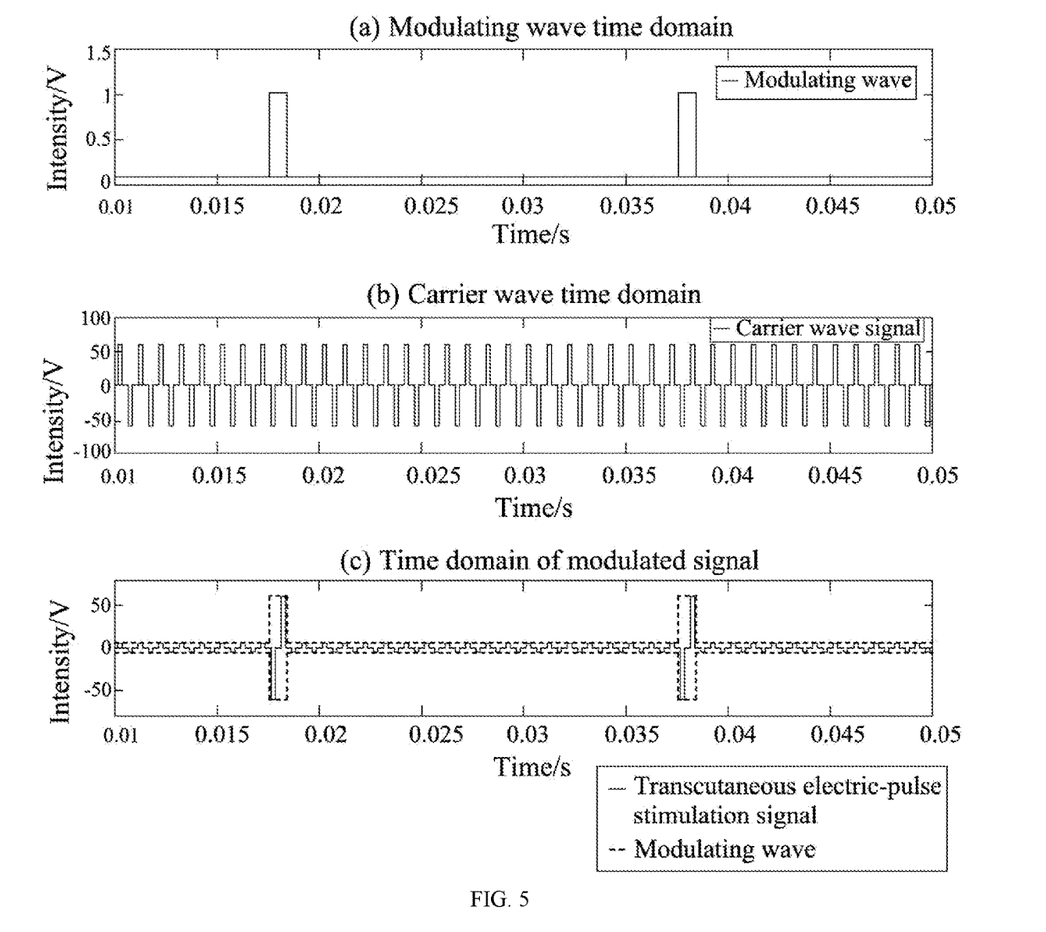
FIG. 5 schematically depicts a modulation of a mid-frequency transcutaneous electric-pulse stimulation signal in accordance with an embodiment of the present disclosure.

FIG. 5 is a modulation process of the mid-frequency transcutaneous electric-pulse stimulation signal.

The first MCU micro-control circuit 113 and the second MCU micro-control circuit 131 can be controlled through the smart phone 40, such that the electric-pulse output circuit 132 can freely output the mid-frequency or low-frequency transcutaneous electric-pulse stimulation signals. When used by the crowd, the action area needs to be deepened, and the mid-frequency transcutaneous electric-pulse stimulation signal is used to replace the low-frequency transcutaneous electric-pulse stimulation signal, maintaining the effect of low frequency parameters and providing a better stimulation effect.

Figure 6:
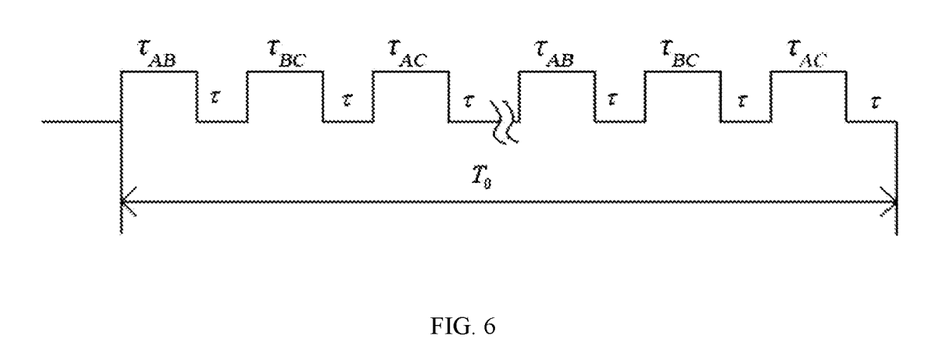
FIG. 6 schematically depicts time series 1 of an electrode sheet group.
Figure 7:
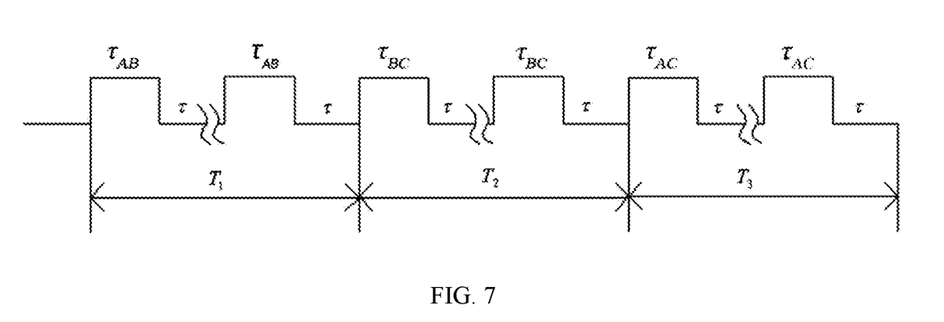
FIG. 7 schematically depicts time series 2 of the electrode sheet group.
Figure 8:
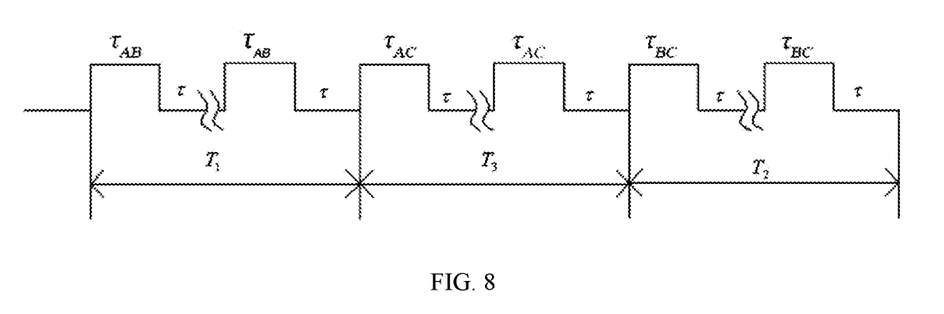
FIG. 8 schematically depicts time series 3 of the electrode sheet group.

As shown in FIGS. 6-8, in order to achieve different stimulating effects, the smart phone 40 controls the first MCU micro-control circuit 113 and the second MCU micro-control circuit 131, such that the electric-pulse output circuit 132 outputs corresponding mid-frequency or low-frequency transcutaneous electric-pulse stimulation signal to the three electrode sheets according to different time series combinations. The time series are shown as follows:

time series 1: $[\tau_{AB}\text{-}\tau\text{-}\tau_{BC}\text{-}\tau\text{-}\tau_{AC}\text{-}\tau]_{T_0}$;

time series 2: $[|\tau_{AB}\text{-}\tau|_{T_1}\text{-}|\tau_{BC}\text{-}\tau|_{T_2}\text{-}|\tau_{AC}\text{-}\tau|_{T_3}]$; and time series 3: $[|\tau_{AB}\text{-}\tau|_{T_1}\text{-}|\tau_{AC}\text{-}\tau|_{T_3}\text{-}|\tau_{BC}\text{-}\tau|_{T_2}]$;

where $\tau_{AB}$ is time for the electrode sheet A and the electrode sheet B to output an electric pulse, and is 3-5 seconds;

$\tau_{BC}$ is time for the electrode sheet B and the electrode sheet C to output an electric pulse, and is 3-5 seconds;

$\tau_{AC}$ is time for the electrode sheet A and the electrode sheet C to output an electric pulse, and is 3-5 seconds;

$\tau$ is time when the electrode sheet A, the electrode sheet B and the electrode sheet C have no output, and is 1-2 seconds;

$T_0$ is time of an output loop of the electrode sheet A, the electrode sheet B and the electrode sheet C in sequence in the time series 1, and is 45-90 min;

$T_1$ is time of an output loop of the electrode sheet A and the electrode sheet B in the time series 2 and the time series 3, and is 15-30 min;

$T_2$ is time of an output loop of the electrode sheet B and the electrode sheet C in the time series 2 and the time series 3, and is 15-30 min;

$T_3$ is time of an output loop of the electrode sheet A and the electrode sheet C in the time series 2 and the time series 3, and is 15-30 min.

Figure 10:
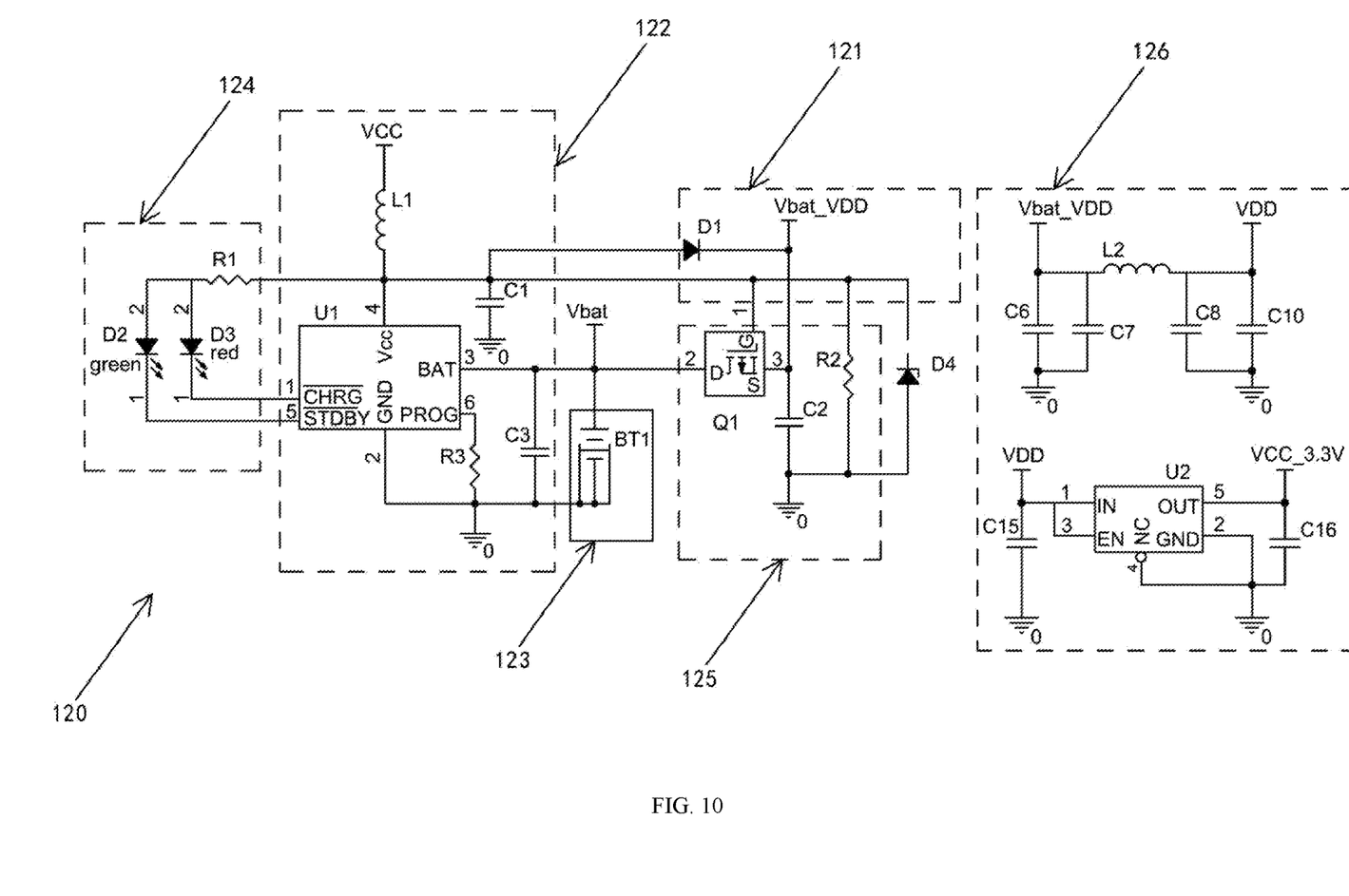
FIG. 10 is a circuit diagram of a power supply module in FIG. 2.

As shown in FIGS. 2 and 10, the power supply module 120 supplies power for the control module 110 and the output module 130. The charging management circuit 122 can use various charging management chips. In some embodiments, the U1 chip is a charging management chip TP404X (Nanjing Top Power ASIC Co., Ltd., China) or a charging management chip LTC404X (Linear Technology Corporation, US). The chips have a function of automatically terminating the charging cycle and recycling recharging. L1 and C1 can filter out the instantaneous surge when the charging power source is plugged in to protect the power supply module 120.

The charging indication circuit 124 indicates a charging state of the system. A charging state is represented by red, and a fully charged state is represented by green.

The power path management circuit 125 uses a P-channel enhanced metal-oxide-semiconductor (MOS) field-effect transistor to manage the power supply of the system. When the rechargeable battery 123, such as a polymer lithium battery, is over-discharged and working with a load, a protection board of the rechargeable battery 123 will be in a stopped state, such that the rechargeable battery 123 is failed to charge. In addition, frequent charging/discharging and performing the charging and discharging at the same time will affect the service life of the rechargeable battery 123. Therefore, when the rechargeable battery 123 is charged by the power path management circuit 125, the therapeutic apparatus is only powered by a power supply connected to the charging port 121.

When the charging port 121 is not connected to a charging power source, the MOS field-effect transistor is turned on and the therapeutic apparatus is powered by the rechargeable battery 123. When the charging port 121 is connected to a charging power source, the MOS field-effect transistor Q1 is turned off and the therapeutic apparatus is powered by the charging power source. D4 is a voltage regulator tube to avoid damage to a charging management chip when the charging port 121 is connected to a power source greater than a maximum input voltage of the charging management chip. The charge management chip is the charge management chip of the charging management circuit 122.

The power conversion circuit 126 converts a voltage of the rechargeable battery 123 into an operating voltage of the control module 110 and the output module 130.

Figure 9:
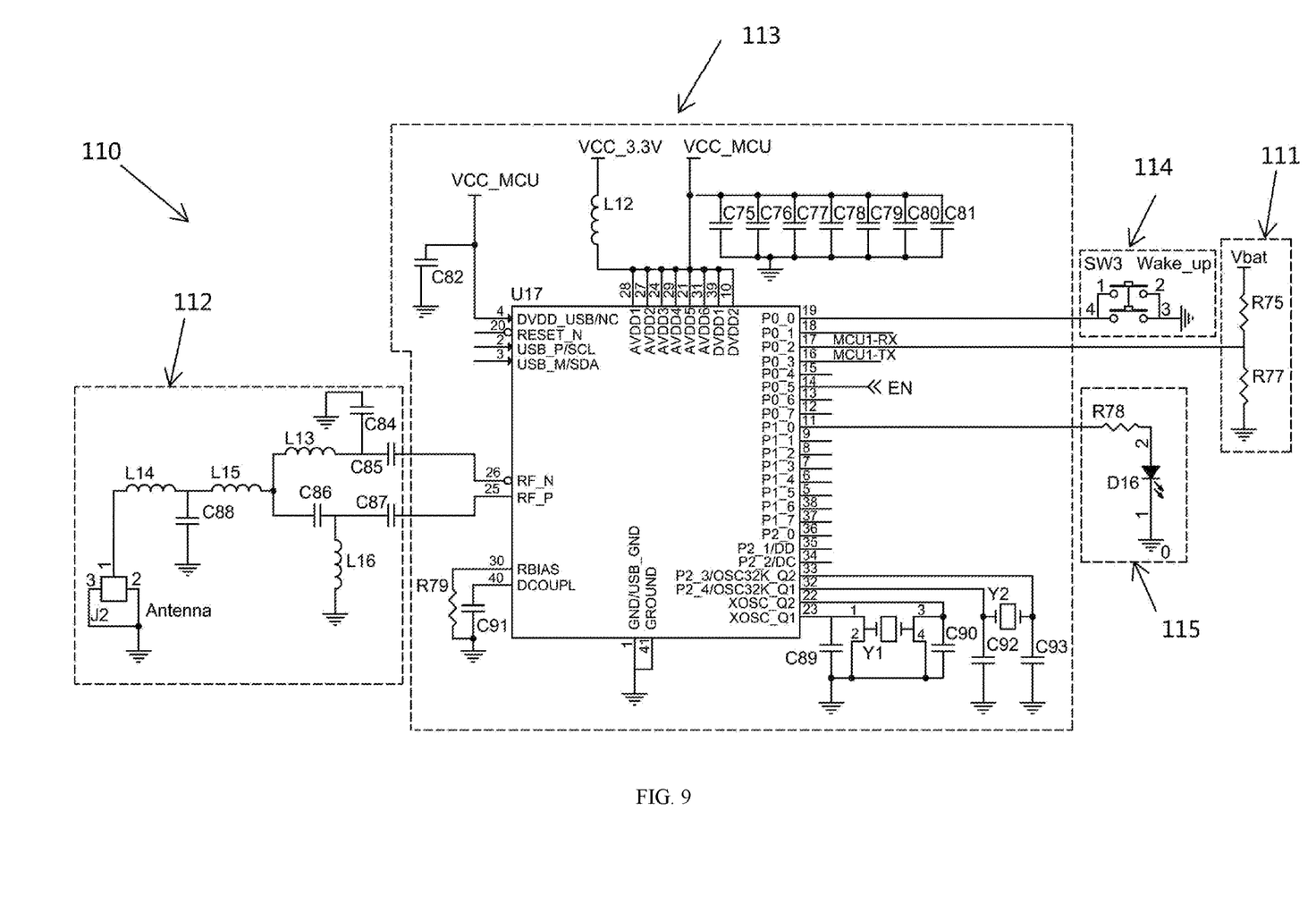
FIG. 9 is a circuit diagram of a control module in FIG. 2.

As shown in FIGS. 2 and 9, the control module 110 includes the first MCU micro-control circuit 113, a power measuring circuit 111, a work indication circuit 115, the switch circuit 114 and the Bluetooth communication circuit 112. A MCU chip (U17) in the first MCU micro-control circuit 113 is a CC254X Bluetooth chip (Texas instruments incorporated, US). The Bluetooth communication circuit 112 includes a 2.4 G Bluetooth antenna and a balun. The balun is a packaged LFB182G45BG2D280 balun chip or a balun circuit matched by capacitance and inductance. The balun converts a single-ended signal into a differential signal, and forms a communication connection between the control module 110 and the smart phone 40.

The switch circuit 114 and the work indication circuit 115 is configured to control the switch of the control module 110 and indicate a working state thereof. The power measuring circuit 111 is configured to measure the power of the rechargeable battery 123.

Figure 11:
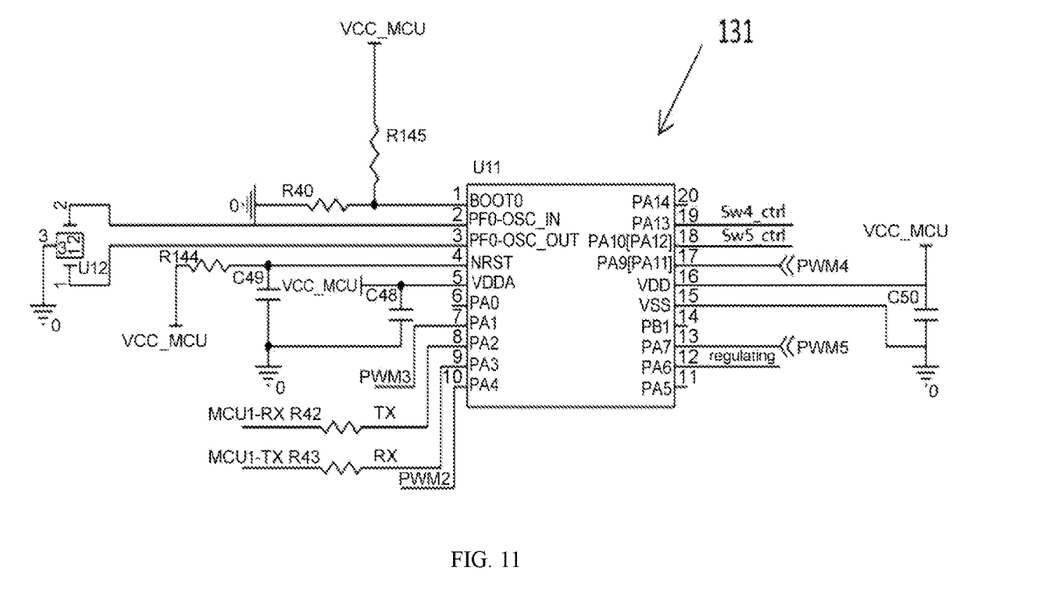
FIG. 11 is a circuit diagram of a second MCU micro-control circuit in FIG. 2.

FIG. 11 is a circuit diagram of the second MCU micro-control circuit 131, in which the MCU chip is U11 (STM32F070X) and outputs pulse signals (PWM4, PWM5), pulse signals (PWM2, PWM3) and a voltage regulation control signals (regulating) to the corresponding electric-pulse output circuit 132, the electric-pulse conversion circuit 135 and the voltage regulation circuit 134.

Figure 12:
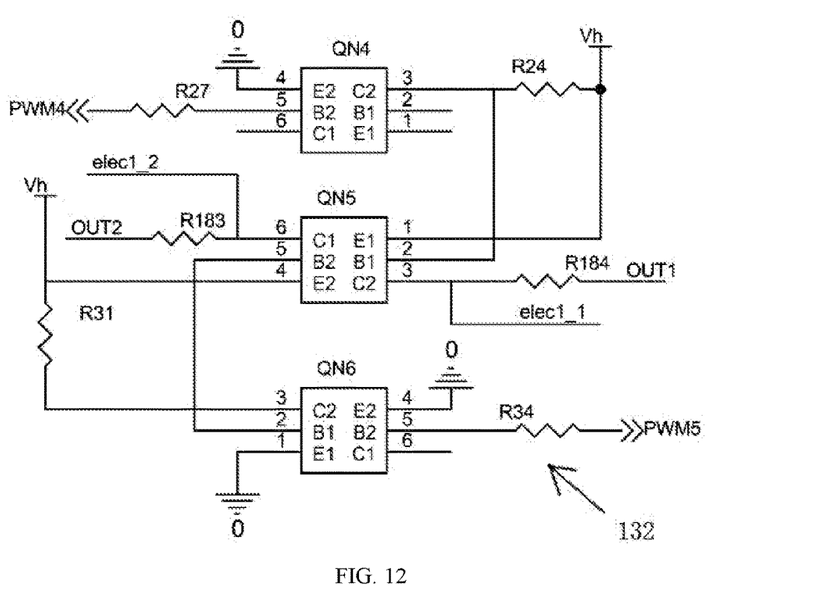
FIG. 12 is a circuit diagram of an electric-pulse output circuit in FIG. 2.
Figure 15:
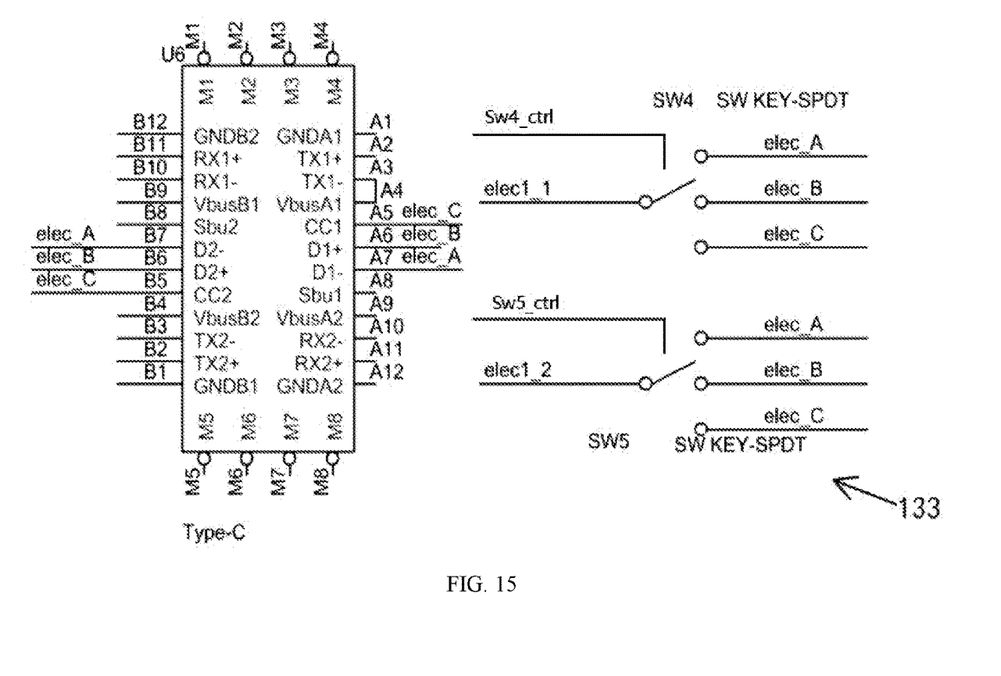
FIG. 15 is a circuit diagram of a Type-C output port circuit in FIG. 2.

FIG. 12 is a circuit diagram of the electric-pulse output circuit 132, in which QN4 and QN6 are NPN transistors, and QN5 is a PNP transistor. The electric-pulse output circuit 132 can output the mid-frequency or low-frequency transcutaneous electric-pulse stimulation signal that meets the aforementioned characterization parameters. Output signals (elec1_1, elec1_2) are selected and switched by SW4 and SW5 (such as a LTC20X multi-channel analog switch of Analog Devices, Inc., US) in the Type-C output port circuit 133 (the switching control can be controlled by Sw4 ctrl and Sw5 ctrl signals output by the second MCU micro-control circuit 131), and then are output by a Type-C port to the electrode sheet A, the electrode sheet B and the electrode sheet C (elec_A, elec_B, elec_C). The Type-C output port circuit 133 is shown in FIG. 15.

Figure 13:
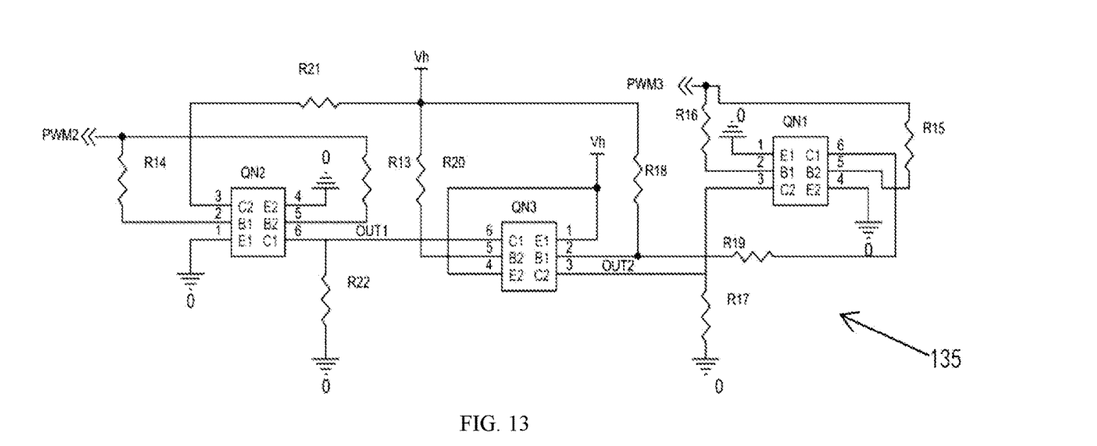
FIG. 13 is a circuit diagram of the electric-pulse conversion circuit in FIG. 2.

FIG. 13 is a circuit diagram of the electric-pulse conversion circuit 135, in which QN1 and QN2 are NPN transistors, and QN3 is a PNP transistor. A pulse signal output by the second MCU micro-control circuit 131 is converted into a modulating wave and output to the electric-pulse output circuit 132.

Figure 14:
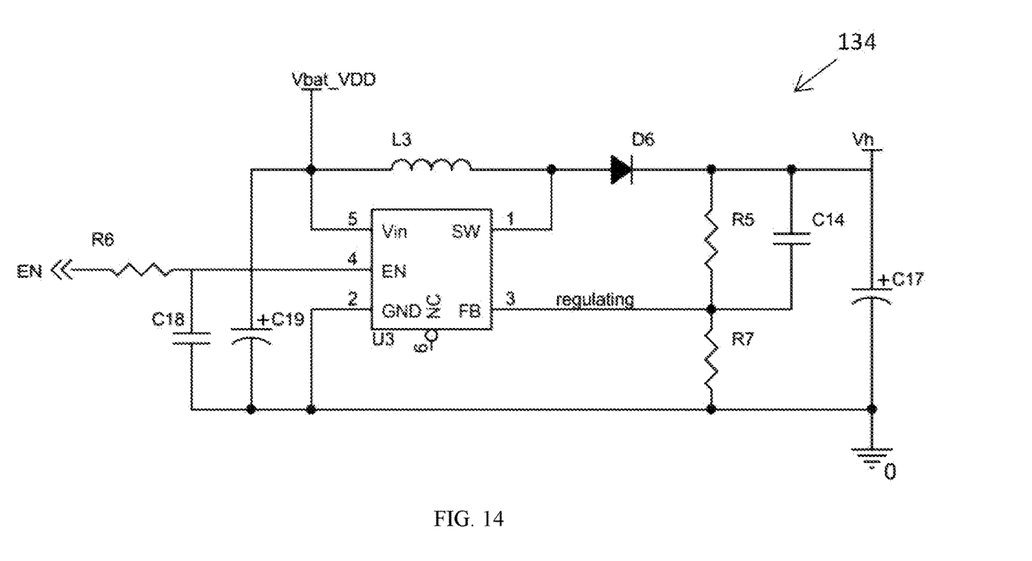
FIG. 14 is a circuit diagram of the voltage regulation circuit in FIG. 2.

FIG. 14 is a circuit diagram of the voltage regulation circuit 134. The second MCU micro-control circuit 131 outputs a regulating control signal (regulating) to U3 (MT and LT chips), and regulates an output power Vh to the electric-pulse output circuit 132 and the electric-pulse conversion circuit 135.

The control terminal used herein is the smart phone 40, which sets the main characteristic parameters of the carrier signal and the modulating wave through an installed application. The characteristic parameters include the mid-frequency transcutaneous electric-pulse stimulation signal or low-frequency transcutaneous electric-pulse stimulation signal, stimulation intensity and stimulation time. The mid-frequency transcutaneous electric-pulse stimulation signal or low-frequency transcutaneous electric-pulse stimulation signal is output by the electric-pulse output circuit 132, and stimulates relevant acupoints such as Zhongzhu acupoint and Tinggong acupoint and Yifeng acupoint of human body through the electrode sheet group 20. The stimulation effect can be optimized through controlling different time series combination of the electrode sheet group 20. It should be noted that the control terminal of the therapeutic apparatus includes but not is limited to various intelligent electronic devices such as tablet computers, smart bracelets and artificial intelligence devices, and remote control instruments controlled by Bluetooth communication.

It should be noted that the presented embodiments are only preferred embodiments of the present disclosure. The embodiments are illustrative, and not intended to limit the scope of the present disclosure. Modifications and replacements made by those skilled in the art without departing from the spirit of this disclosure should fall within the scope of the present disclosure.

What is claimed is:

1. An apparatus for treating tinnitus through stimulating multiple acupoints with a multi-electrode electric pulse based on Bluetooth control, comprising:
   a control terminal;
   a main body;
   an electrode wire; and
   an electrode sheet group connected to the electrode wire;
   wherein the electrode sheet group comprises at least three electrode sheets;
   the main body comprises a control module, a power supply module and an output module; the power supply module and the output module are electrically connected to the control module, respectively; the control module comprises a first microcontroller unit (MCU) micro-control circuit and a Bluetooth communication circuit; the Bluetooth communication circuit is electrically connected to the first MCU micro-control circuit; the first MCU micro-control circuit is connected to the power supply module; the first MCU micro-control circuit is wirelessly connected to the control terminal through the Bluetooth communication circuit;
   the output module comprises a second MCU micro-control circuit, a voltage regulation circuit, an electric-pulse conversion circuit, an electric-pulse output circuit and an output port;
   the second MCU micro-control circuit is electrically connected to the first MCU micro-control circuit, the voltage regulation circuit, the electric-pulse conversion circuit and the electric-pulse output circuit; the voltage regulation circuit is electrically connected to the electric-pulse output circuit and the electric-pulse conversion circuit; the electric-pulse output circuit is electrically connected to the electric-pulse conversion circuit and the output port; and the electrode wire is connected to the output port;
   the first MCU micro-control circuit is configured to control the second MCU micro-control circuit to output a pulse signal to the electric-pulse conversion circuit, so as to output a modulating wave through conversion by the electric-pulse conversion circuit; the pulse signal output from the second MCU micro-control circuit to the electric-pulse output circuit is a carrier signal; a transcutaneous electric-pulse stimulation signal output by the electric-pulse output circuit is an electric pulse of the carrier signal after modulated by the modulating wave;
   the modulating wave is a low-frequency pulse signal which is mainly characterized by frequency $f_{low}$, period $T_{low}$ and pulse width $\tau_{low}$;
   the carrier signal is a mid-frequency pulse signal; the mid-frequency pulse signal is a bipolar signal; the mid-frequency pulse signal is mainly characterized by frequency $f_{mid}$, period $T_{mid}$, pulse width $\tau_{mid}$, time difference $\Delta\tau$ between an end of a negative mid-frequency pulse signal and a start of a positive pulse and a mid-frequency pulse signal duty cycle D;
   the transcutaneous electric-pulse stimulation signal is a rectangular voltage pulse or a rectangular current pulse;
   the transcutaneous electric-pulse stimulation signal is characterized by $f_{low}$, $T_{low}$, $\tau_{low}$, $f_{mid}$, $T_{mid}$, $\tau_{mid}$, $\Delta\tau$, the mid-frequency pulse signal duty cycle D, maximum amplitude $A_{max}$ and minimum amplitude $A_{min}$;
   parameters meet the following conditions:

$$f_{low} = 0.1 \sim 100 \text{ Hz}; f_{low} = \frac{1}{T_{low}};$$

$$f_{mid} = 1 \sim 100 \text{ KHz}; f_{mid} = \frac{1}{T_{mid}};$$

$f_{low}=nf_{mid}$; wherein n is a positive integer;

$\tau_{low}>2\tau_{mid}+\Delta\tau$;

wherein $\Delta\tau=T_{mid}(1-2D)$; $\tau_{low}=0.1\sim1$ ms; $\tau_{mid}=D\cdot T_{mid}$; $D=1\%\sim50\%$;

$$\frac{A_{min}}{A_{max}} = 0 \sim 1;$$

and
   the control terminal is configured to control the first MCU micro-control circuit and the second MCU micro-control circuit to allow the electric-pulse output circuit to output a corresponding transcutaneous electric-pulse stimulation signal to an electrode sheet of the at least three electrode sheets according to a time series combination.

2. The apparatus of claim 1, wherein the electrode sheet group comprises an electrode sheet A, an electrode sheet B and an electrode sheet C; the time series combination is shown as follows:

| | |
|---|---|
| $[\tau_{AB}-\tau-\tau_{BC}-\tau-\tau_{AC}-\tau]_{T_0}$; | time series 1: |
| $[\tau_{AB}-\tau\|_{T_1}-\|\tau_{BC}-\tau\|_{T_2}-\|\tau_{AC}-\tau\|_{T_3}]$; and | time series 2: |
| $[\tau_{AB}-\tau\|_{T_1}-\|\tau_{AC}-\tau\|_{T_3}-\|\tau_{BC}-\tau\|_{T_2}]$; | time series 3: | wherein $\tau_{AB}$ is time for the electrode sheet A and the electrode sheet B to output an electric pulse, and is 3-5 seconds;
$\tau_{BC}$ is time for the electrode sheet B and the electrode sheet C to output an electric pulse, and is 3-5 seconds;
$\tau_{Ac}$ is time for the electrode sheet A and the electrode sheet C to output an electric pulse, and is 3-5 seconds;
$\tau$ is time when the electrode sheet A, the electrode sheet B and the electrode sheet C have no output, and is 1-2 seconds;
$T_0$ is time of an output loop of the electrode sheet A, the electrode sheet B and the electrode sheet C in sequence in the time series 1, and is 45-90 min;

T₁ is time of an output loop of the electrode sheet A and the electrode sheet B in the time series 2 and the time series 3, and is 15-30 min;

T₂ is time of an output loop of the electrode sheet B and the electrode sheet C in the time series 2 and the time series 3, and is 15-30 min; and T₃ is time of an output loop of the electrode sheet A and the electrode sheet C in the time series 2 and the time series 3, and is 15-30 min.

3. The apparatus of claim 1, wherein $f_{low}$=50 Hz; $f_{mid}$=1 KHz; n=20; $T_{low}$=20 ms; $T_{mid}$=1 ms; $\tau_{low}$=800 us; $\tau_{mid}$=200 us; D=20%; and Δτ=300 us.

4. The apparatus of claim 2, wherein $f_{low}$=50 Hz; $f_{mid}$=1 KHz; n=20; $T_{low}$=20 ms; $T_{mid}$=1 ms; $\tau_{low}$=800 us; $\tau_{mid}$=200 us; D=20%; and Δτ=300 us.

5. The apparatus of claim 3, wherein the power supply module comprises a charging port, a charging management circuit, a rechargeable battery, a power path management circuit and a power conversion circuit electrically connected in sequence; the power supply module further comprises a charging indication circuit; the charging indication circuit is electrically connected to the charging management circuit; and the power path management circuit is electrically connected to the first MCU micro-control circuit.

6. The apparatus of claim 4, wherein the power supply module comprises a charging port, a charging management circuit, a rechargeable battery, a power path management circuit and a power conversion circuit electrically connected in sequence; the power supply module further comprises a charging indication circuit; the charging indication circuit is electrically connected to the charging management circuit; and the power path management circuit is electrically connected to the first MCU micro-control circuit.

7. The apparatus of claim 5, wherein the control module further comprises a power measuring circuit, a switch circuit and a work indication circuit; the power measuring circuit, the switch circuit and the work indication circuit are electrically connected to the first MCU micro-control circuit; and the power measuring circuit is electrically connected to the rechargeable battery.

8. The apparatus of claim 6, wherein the control module further comprises a power measuring circuit, a switch circuit and a work indication circuit; the power measuring circuit, the switch circuit and the work indication circuit are electrically connected to the first MCU micro-control circuit; and the power measuring circuit is electrically connected to the rechargeable battery.

9. The apparatus of claim 7, wherein the control terminal is a smart phone.

10. The apparatus of claim 8, wherein the control terminal is a smart phone.

11. An acupoint stimulating method using the apparatus of claim 1, comprising:
    placing three electrode sheets of the apparatus on Zhongzhu acupoint, Tinggong acupoint and Yifeng acupoint of human body, respectively; and
    outputting, by the electric-pulse output circuit, a corresponding transcutaneous electric-pulse stimulation signal to an electrode sheet of the three electrode sheets according to a time series combination.

12. An acupoint stimulating method using the apparatus of claim 2, comprising:
    placing three electrode sheets of the apparatus on Zhongzhu acupoint, Tinggong acupoint and Yifeng acupoint of human body, respectively; and
    outputting, by the electric-pulse output circuit, a corresponding transcutaneous electric-pulse stimulation signal to an electrode sheet of the three electrode sheets according to a time series combination.

\* \* \* \* \*